(12) United States Patent
Rhee et al.

(10) Patent No.: US 7,914,802 B2
(45) Date of Patent: Mar. 29, 2011

(54) MUCOSAL VACCINE ADJUVANTS CONTAINING BACTERIAL FLAGELLINS AS AN ACTIVE COMPONENT

(75) Inventors: Joon-Haeng Rhee, Gwangju (KR); Shee-Eun Lee, Gwangju (KR); Soo-Young Kim, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 133 days.

(21) Appl. No.: 10/585,880

(22) PCT Filed: Jan. 12, 2005

(86) PCT No.: PCT/KR2005/000103
§ 371 (c)(1),
(2), (4) Date: May 3, 2007

(87) PCT Pub. No.: WO2005/070455
PCT Pub. Date: Aug. 4, 2005

(65) Prior Publication Data
US 2008/0069844 A1 Mar. 20, 2008

(30) Foreign Application Priority Data
Jan. 12, 2004 (KR) .................. 10-2004-0001974

(51) Int. Cl.
*A61K 45/00* (2006.01)
*A61K 39/02* (2006.01)
*C07K 14/00* (2006.01)
*C07K 17/00* (2006.01)
*C07K 1/00* (2006.01)

(52) U.S. Cl. ................... 424/282.1; 424/190.1; 530/350

(58) Field of Classification Search ......................... None
See application file for complete search history.

(56) References Cited

FOREIGN PATENT DOCUMENTS

| WO | 02085933 A1 | 10/2002 |
| WO | WO02085933 A1 * | 10/2002 |
| WO | 2004022092 A2 | 3/2004 |

OTHER PUBLICATIONS

McSorley et al. 2002 Journal of Immunology vol. 169 pp. 3914-3919.*
Wu et al 1989 Proc. Natl Acad Science USA vol. 86 pp. 4726-4730.*
Kim et al Biochemical and Biophysical Research Communications 304 (2003) pp. 405-410.*
Amaro et al Current Microbiology vol. 25 (1992) pp. 99-104.*
Cuadros C. et al, "Flagellin fusion proteins as adjuvants or vaccines induce specific immune responses." *In Infect. Iuumn.*, vol. 27, No. 5, May 2004, pp. 2810-2816.
Sbrogio-Almeida M.E., et al., "Host and bacterial factors affecting induction of immune responses to flagellin expressed by attenuated *Salmonella* vaccine strains," *In Infect. Immun.*, vol. 72, No. 5, May 2004, pp. 2546-2555.
Kodama C., et al., "*Salmonella* flagellin is not a dominant protective antigen in oral immunization with attenuated live vaccine strains," *In Infect. Immun.*, vol. 72, No. 4, Apr. 2004, pp. 2449-2451.
Jiang, Zi-Hua, et al., "Synthetic Vaccines: The Role of Adjuvants in Immune Targeting," Current Medicinal Chemistry, 2003, 10, 1423-1439.
McSorley, S.J., et al., "Bacterial Flagellin Is An Effective Adjuvant for CD4+ T Cells in Vivo," J. of Immunology, 169: 3914-3919 (2002).
Smith K D et al: "Toll-like receptor 5 recognizes a conserved site on flagellin required for protofilament formation and bacterial motility" Nature Immunology, Nature Publishing Group, GB, vol. 4, No. 12, Dec. 1, 2003, pp. 1247-1253, XP002999619, ISSN: 1529-2908 *p. 1248*.
Database UniProt [Online] Mar. 1, 2003, "SubName: Full=Flagellin FlaE;" XP002526974 retrieved from EBI accession No. UNIPROT.
Supplementary European Search Report dated Jul. 7, 2009.
European Patent Office, Office Action issued in application 05 721 779.6, dated Nov. 5, 2009.
Gov't of India Patent Office, First Examination Report issued in application No. 806/MUMNP/2006 dated Dec. 31, 2009.
Wu, Jane Y. et al., "Expression of immunogenic epitopes of hepatitis B surface antigen with hybrid flagellin proteins by a vaccine strain of *Salmonella*," Proc. Natl. Acad. Science, USA, vol. 86, pp. 4726-4730, Jun. 1989.
Chinese Office Action issued in application No. 200580002321.4 on Mar. 11, 2010 with English translation.
Indian Patent Office Examination Report issued in counterpart Indian Application No. 806/MUMNP/2006 dated Jul. 8, 2010.

* cited by examiner

*Primary Examiner* — Robert A. Zeman
*Assistant Examiner* — Nina A Archie
(74) *Attorney, Agent, or Firm* — Sughrue Mion, PLLC

(57) ABSTRACT

The present invention relates to mucosal vaccine adjuvants containing flagellins, the structural component of flagella, originated from *Vibrio vulnificus, Salmonella typhimurium*, and *Listeria monocytogenes* as an active component.

3 Claims, 4 Drawing Sheets

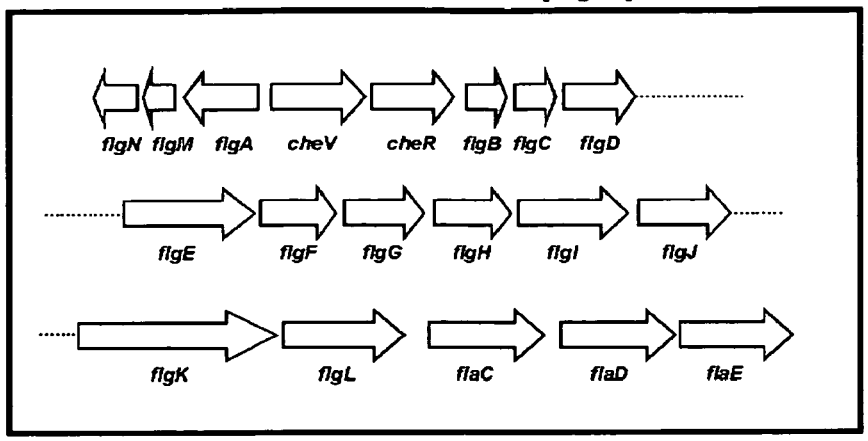
[Fig. 1]
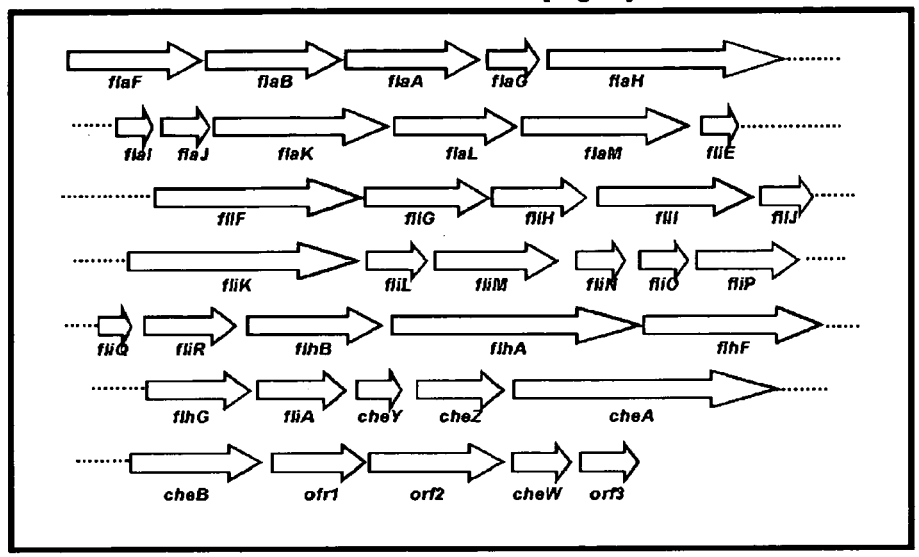
[Fig. 2]
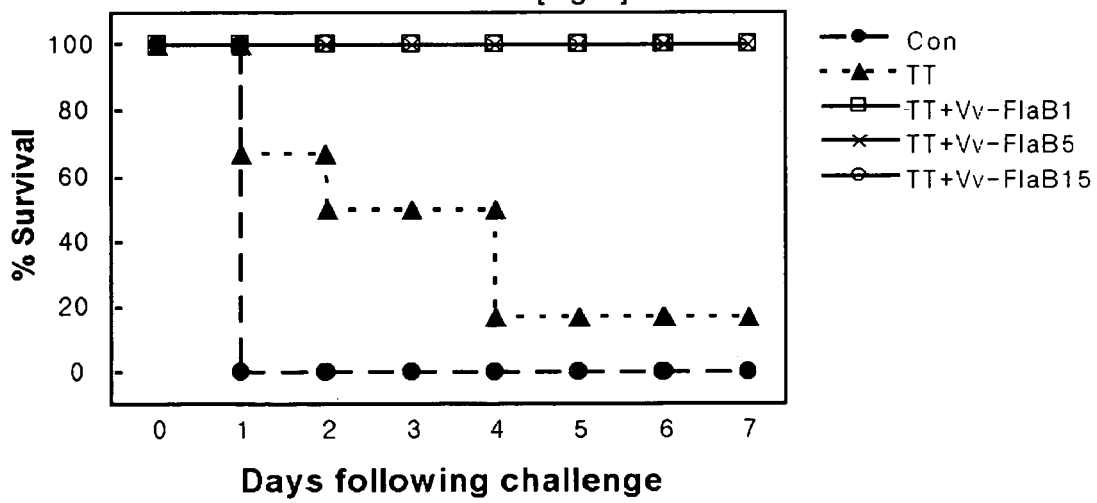
[Fig. 3]

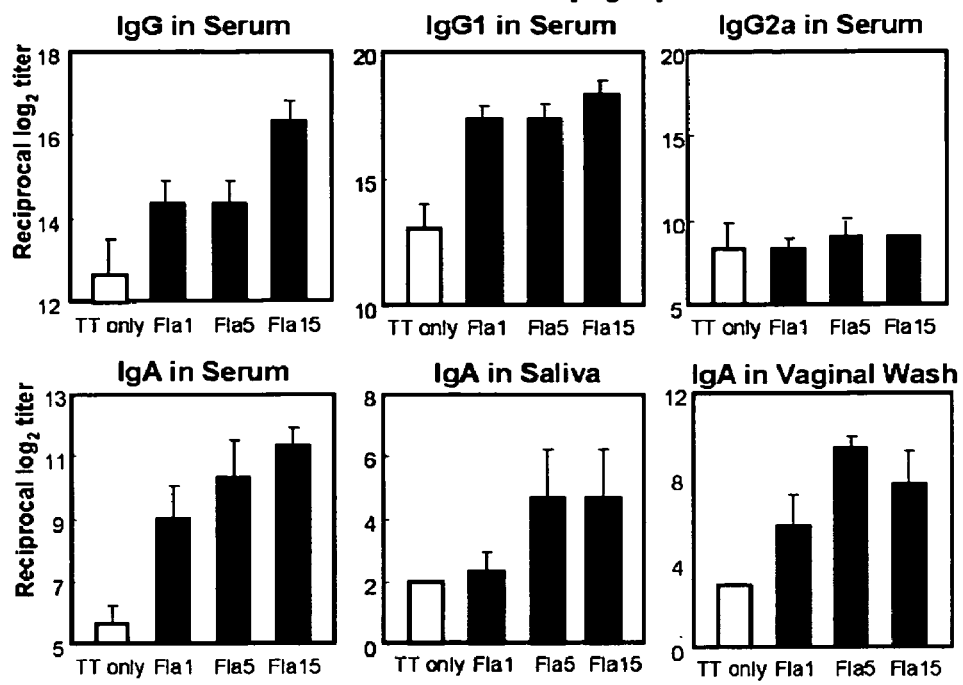
[Fig. 4]
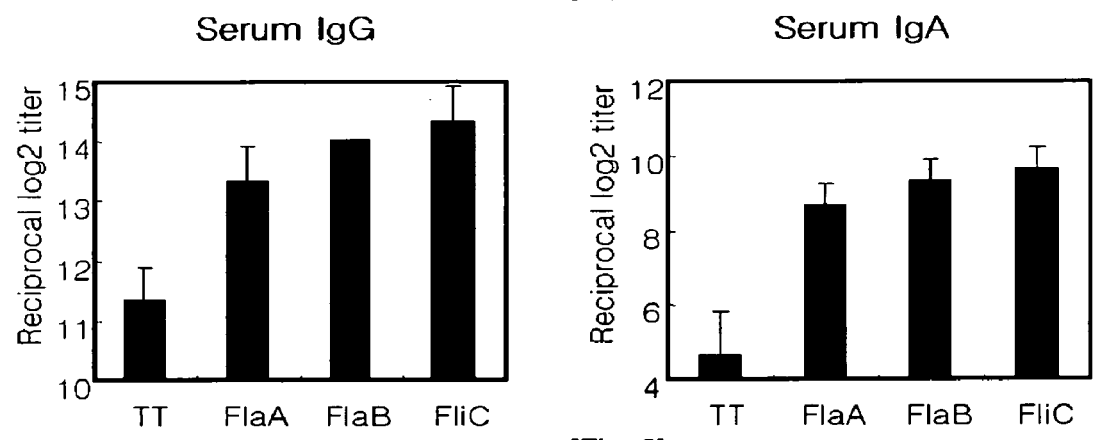
[Fig. 5]
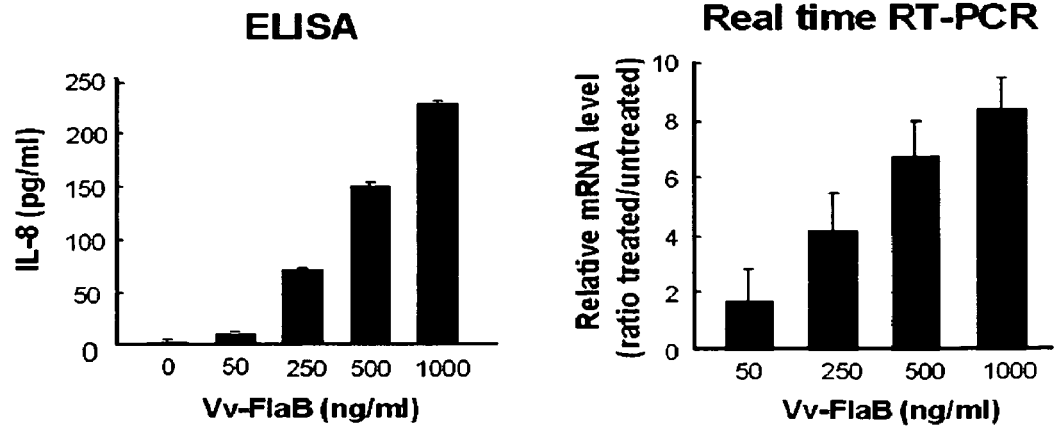
[Fig. 6]

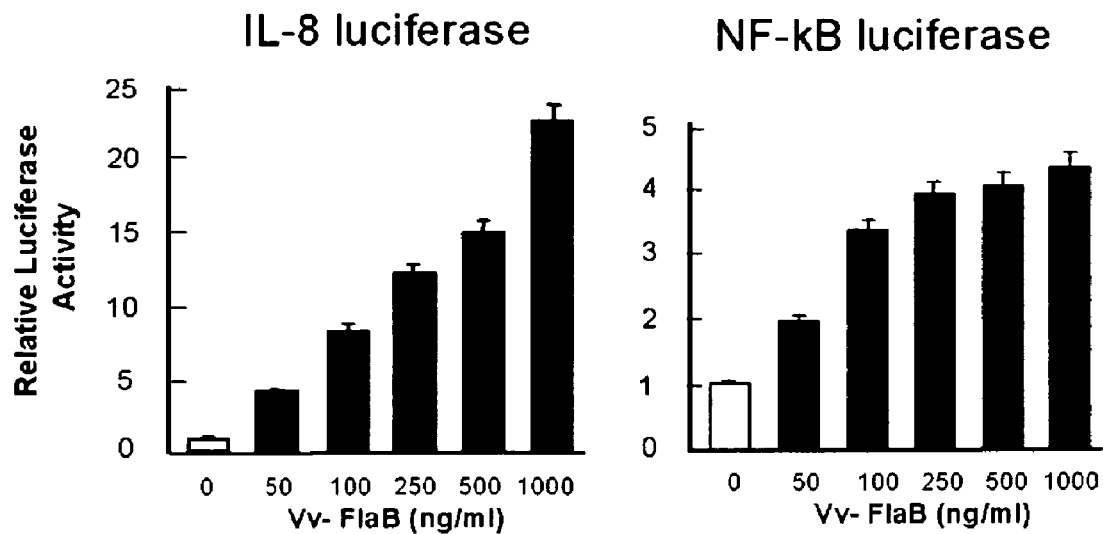
[Fig. 7]
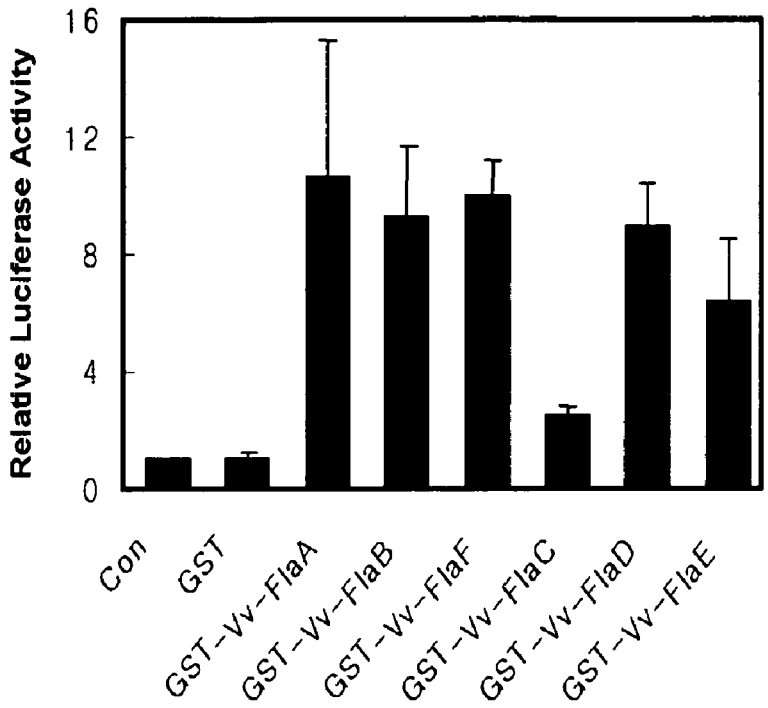
[Fig. 8]

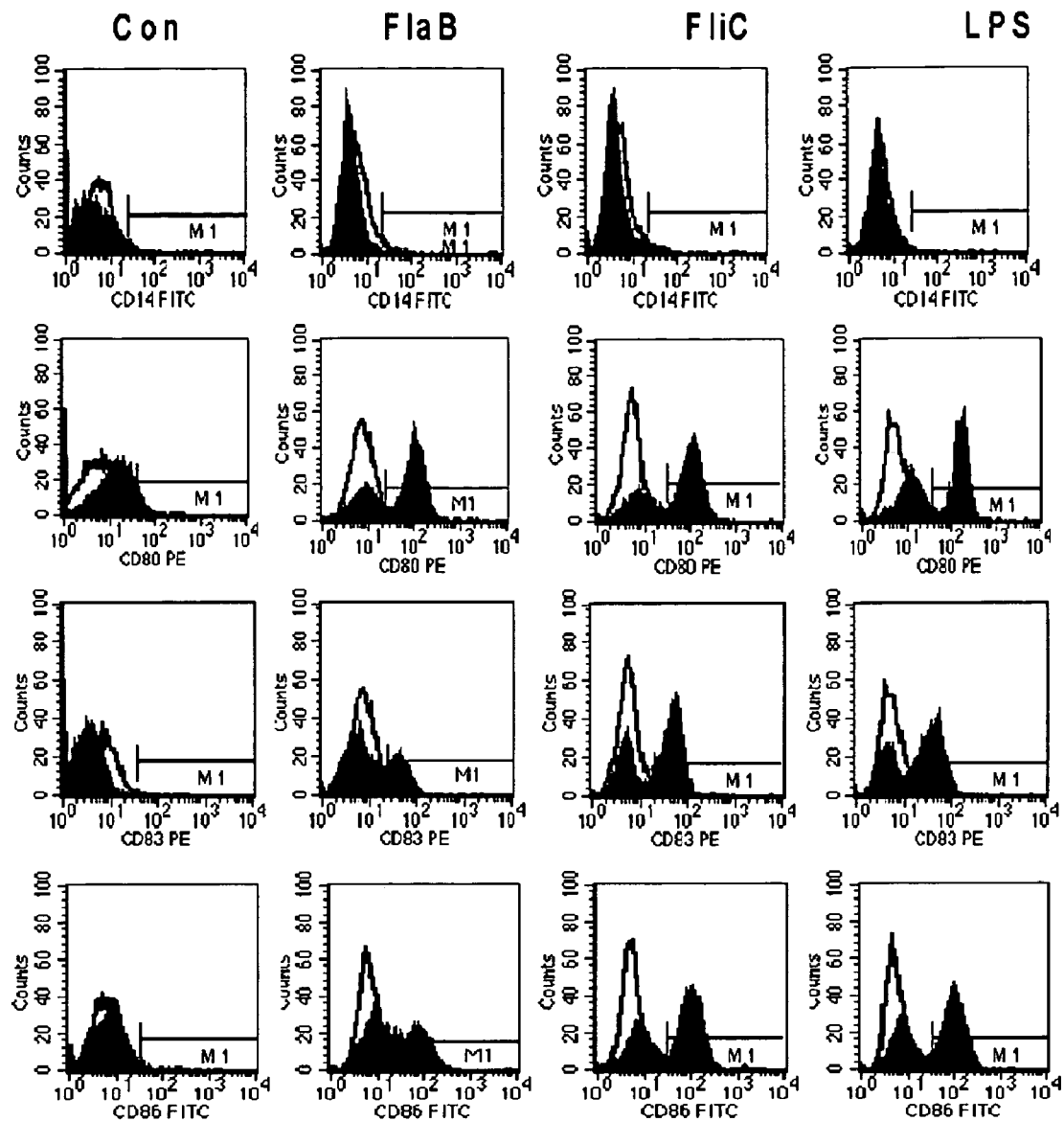
[Fig. 9]

SEQUENCE LISTING

```
<160> NUMBER OF SEQ ID NOS: 18

<210> SEQ ID NO 1
<211> LENGTH: 1131
<212> TYPE: DNA
<213> ORGANISM: Vibrio vulnificus
```

<400> SEQUENCE: 1

```
atggctatca atgtaaacac taacgtgtca gcaatgaccg cacagcgtta cctaaaccag    60
gccgctgaag gtcaacaaaa atcaatggag cgtttgtctt cgggctataa aatcaatagc   120
gcgaaagatg atgctgcagg tctacaaatt tctaaccgtt tgaactcgca aagccgtggt   180
ctcgacatgg cggttaaaaa tgccaacgat ggtatctcta ttgcacagac tgctgaaggt   240
gcaatgacag agaccaccaa catcctacaa cgtatgcgtg accttgcctt gcaatcgtct   300
aacggttcga actctcgttc tgaacgcgtg gcgattcaag aagaagtgtc agcgttgaac   360
caagaactta accgtatcgc agagacaacc tcttttggtg gtaacaaact ccttaacggt   420
acgtacggtt ctcaatcttt ccaaatcggt gctgactctg gtgaagctgt gatgctttct   480
atgggtaacc ttcgttcaga tacagacgcg atgggcggct tgagctacaa atctgaagaa   540
ggcgtaggcg cagattggcg tgtaagcgac aacactgact tcacgatgtc ttatgtgaat   600
aagcaaggtg aagaaaaaga gatcacagtc aacgccaaag cgggtgacga tcttgaagaa   660
ctggcgactt acatcaacgg tcaaaacgat gatgtgaaag cgtcggtcgg tgaaggcggc   720
aaactgcagc tattcgcttc taaccaacgt gtagaaggtg aagtggaatt cggtggtggt   780
ctagcgtctg agttgaacat tggtgatggc accaaaacca atgtgagcaa cattgatgtc   840
acgacggttg ctggctctca agaagcagta gcgatcattg atggcgcatt gaaatcggta   900
gacagtgagc gtgcctctct aggtgcattc caaaaccgtt tcaaccatgc aatcagcaac   960
ctaagcaaca tcaatgagaa cgtaaacgct tcgagcagcc gtatcaagga taccgactac  1020
gcgaaagaaa cgactcagat gactaagacg caaattctgc agcaggcgag tacttctatc  1080
ctggcgcagg cgaagcagtc accatctgca gctcttagct tgttgggcta a           1131
```

<210> SEQ ID NO 2  
<211> LENGTH: 376  
<212> TYPE: PRT  
<213> ORGANISM: Vibrio vulnificus

<400> SEQUENCE: 2

```
Met Ala Ile Asn Val Asn Thr Asn Val Ser Ala Met Thr Ala Gln Arg
 1               5                  10                  15

Tyr Leu Asn Gln Ala Ala Glu Gly Gln Gln Lys Ser Met Glu Arg Leu
            20                  25                  30

Ser Ser Gly Tyr Lys Ile Asn Ser Ala Lys Asp Asp Ala Ala Gly Leu
        35                  40                  45

Gln Ile Ser Asn Arg Leu Asn Ser Gln Ser Arg Gly Leu Asp Met Ala
    50                  55                  60

Val Lys Asn Ala Asn Asp Gly Ile Ser Ile Ala Gln Thr Ala Glu Gly
65                  70                  75                  80

Ala Met Thr Glu Thr Thr Asn Ile Leu Gln Arg Met Arg Asp Leu Ala
                85                  90                  95

Leu Gln Ser Ser Asn Gly Ser Asn Ser Arg Ser Glu Arg Val Ala Ile
            100                 105                 110

Gln Glu Glu Val Ser Ala Leu Asn Gln Glu Leu Asn Arg Ile Ala Glu
        115                 120                 125

Thr Thr Ser Phe Gly Gly Asn Lys Leu Leu Asn Gly Thr Tyr Gly Ser
    130                 135                 140

Gln Ser Phe Gln Ile Gly Ala Asp Ser Gly Glu Ala Val Met Leu Ser
145                 150                 155                 160

Met Gly Asn Leu Arg Ser Asp Thr Asp Ala Met Gly Gly Leu Ser Tyr
```

|   |   |   |   |   | 165 |   |   |   | 170 |   |   |   | 175 |   |
|---|---|---|---|---|---|---|---|---|---|---|---|---|---|---|
| Lys | Ser | Glu | Glu | Gly | Val | Gly | Ala | Asp | Trp | Arg | Val | Ser | Asp | Asn | Thr |
|   |   |   | 180 |   |   |   |   | 185 |   |   |   |   | 190 |

Asp Phe Thr Met Ser Tyr Val Asn Lys Gln Gly Glu Glu Lys Glu Ile
        195                 200                 205

Thr Val Asn Ala Lys Ala Gly Asp Asp Leu Glu Glu Leu Ala Thr Tyr
    210                 215                 220

Ile Asn Gly Gln Asn Asp Asp Val Lys Ala Ser Val Gly Glu Gly Gly
225                 230                 235                 240

Lys Leu Gln Leu Phe Ala Ser Asn Gln Arg Val Glu Gly Glu Val Glu
                245                 250                 255

Phe Gly Gly Gly Leu Ala Ser Glu Leu Asn Ile Gly Asp Gly Thr Lys
            260                 265                 270

Thr Asn Val Ser Asn Ile Asp Val Thr Thr Val Ala Gly Ser Gln Glu
        275                 280                 285

Ala Val Ala Ile Ile Asp Gly Ala Leu Lys Ser Val Asp Ser Glu Arg
    290                 295                 300

Ala Ser Leu Gly Ala Phe Gln Asn Arg Phe Asn His Ala Ile Ser Asn
305                 310                 315                 320

Leu Ser Asn Ile Asn Glu Asn Val Asn Ala Ser Ser Arg Ile Lys
                325                 330                 335

Asp Thr Asp Tyr Ala Lys Glu Thr Thr Gln Met Thr Lys Thr Gln Ile
            340                 345                 350

Leu Gln Gln Ala Ser Thr Ser Ile Leu Ala Gln Ala Lys Gln Ser Pro
        355                 360                 365

Ser Ala Ala Leu Ser Leu Leu Gly
    370                 375

<210> SEQ ID NO 3
<211> LENGTH: 1133
<212> TYPE: DNA
<213> ORGANISM: Vibrio vulnificus

<400> SEQUENCE: 3

```
atggcagtga atgtaaatac aaacgtagca gcaatgacag cacagcgtta cctgaataac      60
gcaaacagcg cacaacaaac ttcgatggag cgtctgtctt caggtttcaa atcaacagt     120
gcaaaagatg acgcagccgg tctgcaaatc tctaaccgct gaacgtaca aagtcgcggt     180
ctagacgttg cggtacgtaa cgccaacgac ggtatctcaa tcgcacaaac cgcagaaggt     240
gcgatgaacg agaccaccaa catcctacaa cgtatgcgtg acctatctct acaatccgcg     300
aacggctcaa actcaaaatc agagcgcgtg gcgattcaag aagaagtgac agcattgaat     360
gacgagctaa accgtattgc agaaaccacg tcttttggtg gtaacaagct gctaaacggt     420
acttacggca cgaaagcaat gcaaattggt gcggataacg gtgaagcggt catgctttca     480
ctgaaagaca tgcgctctga caacgtgatg atgggcggcg tgagctacca agctgaagaa     540
ggcaaagaca gaactggaa tgtggccgca ggcgacaacg acttgacgat tgcactgaca     600
gacagctttg gtaacgagca agagatcgaa atcaacgcga aagcgggtga tgacatcgaa     660
gagctagcga cgtacatcaa cggtcaaact gaccttgtaa aagcgtcagt gggtgaaggc     720
ggcaagctac agatctttgc tggtaacaac aaagttcaag gtgaaattgc tttctcaggt     780
agcctagctg gtgaacttgg cctaggcgaa ggcaaaaacg tcacggtaga cacgattgac     840
gtgacaaccg tacaaggtgc gcaagagtcg tagcgattg tggatgcggc actgaaatac     900
gtagacagcc accgtgcaga gctgggtgca ttccagaacc gtttcaacca tgcaatcagc     960
```

```
aacttggaca acatcaacga aaacgtgaac gcgtcgaaga gccgaatcaa agataccgac    1020
ttcgcgaaag aaacgactca gttgaccaag acacaaattc tatcgcaagc atcaagttcc    1080
attcttgcgc aagcgaaaca agcgccaaac tcagcgctaa gtctactagg cta           1133
```

```
<210> SEQ ID NO 4
<211> LENGTH: 375
<212> TYPE: PRT
<213> ORGANISM: Vibrio vulnificus

<400> SEQUENCE: 4

Met Ala Val Asn Val Asn Thr Asn Val Ala Ala Met Thr Ala Gln Arg
 1               5                  10                  15

Tyr Leu Asn Asn Ala Asn Ser Ala Gln Gln Thr Ser Met Glu Arg Leu
                20                  25                  30

Ser Ser Gly Phe Lys Ile Asn Ser Ala Lys Asp Asp Ala Ala Gly Leu
            35                  40                  45

Gln Ile Ser Asn Arg Leu Asn Val Gln Ser Arg Gly Leu Asp Val Ala
        50                  55                  60

Val Arg Asn Ala Asn Asp Gly Ile Ser Ile Ala Gln Thr Ala Glu Gly
 65                 70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
               100                 105                 110

Gln Glu Glu Val Thr Ala Leu Asn Asp Glu Leu Asn Arg Ile Ala Glu
            115                 120                 125

Thr Thr Ser Phe Gly Gly Asn Lys Leu Leu Asn Gly Thr Tyr Gly Thr
        130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350
```

Ile Leu Ser Gln Ala Ser Ser Ser Ile Leu Ala Gln Ala Lys Gln Ala
        355                 360                 365

Pro Asn Ser Ala Leu Ser Leu
        370                 375

<210> SEQ ID NO 5
<211> LENGTH: 1133
<212> TYPE: DNA
<213> ORGANISM: Vibrio vulnificus

<400> SEQUENCE: 5
gtggcgatca ccgttaatac caatgtggca gcacttgtcg cacagcgtca tttgaccagt      60
gcaaccgaca tgctgaatca atccttggag cgtttgtctt cagggaagcg tattaatagt     120
gcaaaagacg atgcggcagg gctgcaaatt tcgaatcgtc ttcagtcgca aatgcgtggt     180
ttagatatcg cggtgcgaaa tgccaatgat ggcatctcca ttatgcagac tgcggaaggg     240
gcaatgaatg aaaccactaa tattctccaa aggatgcgtg atctttcatt gcaatccgcc     300
aatggttcca atagctatgc tgaaagaata gccttacaag aagaaatgac cgcgttaaat     360
gacgagttga accgtatcgc agaaaccacc tcgttcggtg gcgtaaaatt gctcaatggt     420
tcctttggct cggctgcctt tcagataggg gcagcgtcag gtgaagcggt gcaagtgcaa     480
ctgaagtcga tgcgcagtga tggtattgat atgggtggct tcagttacat tgcaaacgga     540
cgtgcccgtt ctgattggca agtaaaagag ggggcgaatg cgcttagcat gtcattcacg     600
aatcgttttg gtgaaacaga aacgatccaa attaatgcga aagccggcga tgatatcgaa     660
gagcttgcga cctacattaa tggtcagact gacaaagtca cggcatcggt gaatgaagaa     720
ggtcagctac agttgtttat ggccggcgaa gaaacctcag aacgttatcg tttttcagga     780
gacttagcca gtgaactcgg tttgcaacta aaaggttacg atgcggtgga taatatcgac     840
attacttctg tcggtggcgc tcaacaagca gtggctgtcc ttgataccgc gatgaaatac     900
gtcgatagtc atcgtgctga gctaggggca tatcaaaacc gcttcagcca tgcgattaat     960
aacctcgaca catccacga aaacttggcg acatcaaaca gtcgcattca agatacagac    1020
tatgcgaagg aaaccacgcg catggtcaaa caacagatcc tacagcaagt cagtacttct    1080
attttggcgc aggcgaaaaa agggccgaat ctcgcgttga ccttgctggg ata           1133

<210> SEQ ID NO 6
<211> LENGTH: 375
<212> TYPE: PRT
<213> ORGANISM: Vibrio vulnificus

<400> SEQUENCE: 6

Val Ala Ile Thr Val Asn Thr Asn Val Ala Ala Leu Val Ala Gln Arg
  1               5                  10                  15

His Leu Thr Ser Ala Thr Asp Met Leu Asn Gln Ser Leu Glu Arg Leu
             20                  25                  30

Ser Ser Gly Lys Arg Ile Asn Ser Ala Lys Asp Asp Ala Ala Gly Leu
         35                  40                  45

Gln Ile Ser Asn Arg Leu Gln Ser Gln Met Arg Gly Leu Asp Ile Ala
     50                  55                  60

Val Arg Asn Ala Asn Asp Gly Ile Ser Ile Met Gln Thr Ala Glu Gly
 65                  70                  75                  80

Ala Met Asn Glu Thr Thr Asn Ile Leu Gln Arg Met Arg Asp Leu Ser
                 85                  90                  95

Leu Gln Ser Ala Asn Gly Ser Asn Ser Tyr Ala Glu Arg Ile Ala Leu

|           |           |           |           |           |           |           |           |           |           |           |           |           |
|-----------|-----------|-----------|-----------|-----------|-----------|-----------|-----------|-----------|-----------|-----------|-----------|-----------|
|           |           | 100       |           |           |           | 105       |           |           |           | 110       |           |           |

Gln Glu Glu Met Thr Ala Leu Asn Asp Glu Leu Asn Arg Ile Ala Glu
115                 120                 125

Thr Thr Ser Phe Gly Arg Lys Leu Leu Asn Gly Ser Phe Gly Ser
130                 135                 140

Ala Ala Phe Gln Ile Gly Ala Ala Ser Gly Glu Ala Val Gln Val Gln
145                 150                 155                 160

Leu Lys Ser Met Arg Ser Asp Gly Ile Asp Met Gly Gly Phe Ser Tyr
                165                 170                 175

Ile Ala Asn Gly Arg Ala Arg Ser Asp Trp Gln Val Lys Glu Gly Ala
                180                 185                 190

Asn Ala Leu Ser Met Ser Phe Thr Asn Arg Phe Gly Glu Thr Glu Thr
                195                 200                 205

Ile Gln Ile Asn Ala Lys Ala Gly Asp Asp Ile Glu Glu Leu Ala Thr
                210                 215                 220

Tyr Ile Asn Gly Gln Thr Asp Lys Val Thr Ala Ser Val Asn Glu Glu
225                 230                 235                 240

Gly Gln Leu Gln Leu Phe Met Ala Gly Glu Glu Thr Ser Gly Thr Leu
                245                 250                 255

Ser Phe Ser Gly Asp Leu Ala Ser Glu Leu Gly Leu Gln Leu Lys Gly
                260                 265                 270

Tyr Asp Ala Val Asp Asn Ile Asp Ile Thr Ser Val Gly Gly Ala Gln
                275                 280                 285

Gln Ala Val Ala Val Leu Asp Thr Ala Met Lys Tyr Val Asp Ser His
290                 295                 300

Arg Ala Glu Leu Gly Ala Tyr Gln Asn Arg Phe Ser His Ala Ile Asn
305                 310                 315                 320

Asn Leu Asp Asn Ile His Glu Asn Leu Ala Thr Ser Asn Ser Arg Ile
                325                 330                 335

Gln Asp Thr Asp Tyr Ala Lys Glu Thr Thr Arg Met Val Lys Gln Gln
                340                 345                 350

Ile Leu Gln Gln Val Ser Thr Ser Ile Leu Ala Gln Ala Lys Lys Gly
                355                 360                 365

Pro Asn Leu Ala Leu Thr Leu
                370                 375

<210> SEQ ID NO 7
<211> LENGTH: 1158
<212> TYPE: DNA
<213> ORGANISM: Vibrio vulnificus

<400> SEQUENCE: 7
atggctgtaa cagtaagcac taacgtatcc gcgatgactg cgcaacgtta tctaaacaaa     60
gcgacagatg agttaaacac ctcaatggaa cgtttgtcat ctggtcataa aattaatagc    120
gccaaagatg atgcggccgg tttgcaaatt tctaaccgct taaccgctca gtctcgtggc    180
ctagatgtgg cgatgcgtaa tgccaacgat ggtatctcta tcgctcaaac cgccgaaggg    240
gcgatgaatg aagcgacggc agtcttgcag cgcatgcgtg acttgtcgat tcaatccgcg    300
aacggtacta actcaacgtc tgagcgccaa gcgattcatg aagaagcgag tgctctacaa    360
gacgaaatta ccgtattgc tgaaaccaca tcgtttggtg acgccgtct actgaatggc    420 acctttggtg atgcagcatt ccagattggt tctaactctg gtgaagcgat gattatgggc    480
ttaaccagca tccgtgccga tgatttccgt atgggtggca cgaccttcca gtctgaaaat    540
ggcaaaaaca agattgggaa gtgagcgcg ataacgcag agctgaacat cgtattgcca    600

-continued

```
gagatgggtg aagatgaaga tggcaatgtt atcgatttag aaatcaacat catggcgaaa    660
agcggtgatg atattgaaga attggcaacg tacatcaatg gtcaatcgga ctacatcaac    720
gcatcggtaa gtgaagatgg caagctgcaa atctttgttg ctcaaccaaa tgtgaaaggc    780
gatatctcga tttcgggtag ccttgcctct gaactgggtt tgagtgacga accgattgcg    840
acaacagtac aagatttgga tctgcgtacc gtacaaggtt ctcagaacgc aattagcgtt    900
attgacgcgg cattgaagta cgttgattca caacgtgcgg acttaggtgc aaaacagaac    960
cgtttaagcc acagtattaa taacttggcg aacgttcaag aaaacgttga tgcatcgaac   1020
agccgtatta aagatactga ttttgcgaag gaaacgacgc aaatgacgaa agcacagatt   1080
ttgcaacagg caggtacttc tattcttgct caagcaaaac aattgccaaa ctctgcaatg   1140
tcactattgc agggctaa                                                 1158
```

<210> SEQ ID NO 8
<211> LENGTH: 383
<212> TYPE: PRT
<213> ORGANISM: Vibrio vulnificus

<400> SEQUENCE: 8

```
Met Ala Val Thr Val Ser Thr Asn Val Ser Ala Met Thr Ala Gln Arg
 1               5                  10                  15

Tyr Leu Asn Lys Ala Thr Asp Glu Leu Asn Thr Ser Met Glu Arg Leu
            20                  25                  30

Ser Ser Gly His Lys Ile Asn Ser Ala Lys Asp Asp Ala Ala Gly Leu
        35                  40                  45

Gln Ile Ser Asn Arg Leu Thr Ala Gln Ser Arg Gly Leu Asp Val Ala
    50                  55                  60

Met Arg Asn Ala Asn Asp Gly Ile Ser Ile Ala Gln Thr Ala Glu Gly
65                  70                  75                  80

Ala Met Asn Glu Ala Thr Ala Val Leu Gln Arg Met Arg Asp Leu Ser
                85                  90                  95

Ile Gln Ser Ala Asn Gly Thr Asn Ser Thr Ser Glu Arg Gln Ala Ile
           100                 105                 110

His Glu Glu Ala Ser Ala Leu Gln Asp Glu Ile Asn Arg Ile Ala Glu
       115                 120                 125

Thr Thr Ser Phe Gly Gly Arg Leu Leu Asn Gly Thr Phe Gly Asp
   130                 135                 140

Ala Ala Phe Gln Ile Gly Ser Asn Ser Gly Glu Ala Met Ile Met Gly
145                 150                 155                 160

Leu Thr Ser Ile Arg Ala Asp Asp Phe Arg Met Gly Gly Thr Thr Phe
                165                 170                 175

Gln Ser Glu Asn Gly Lys Asn Lys Asp Trp Glu Val Ser Ala Asp Asn
           180                 185                 190

Ala Glu Leu Asn Ile Val Leu Pro Glu Met Gly Glu Asp Glu Gly
       195                 200                 205

Asn Val Ile Asp Leu Glu Ile Asn Ile Met Ala Lys Ser Gly Asp Asp
   210                 215                 220

Ile Glu Glu Leu Ala Thr Tyr Ile Asn Gly Gln Ser Asp Tyr Ile Asn
225                 230                 235                 240

Ala Ser Val Ser Glu Asp Gly Lys Leu Gln Ile Phe Val Ala Gln Pro
                245                 250                 255

Asn Val Lys Gly Asp Ile Ser Ile Ser Gly Ser Leu Ala Ser Glu Leu
           260                 265                 270
```

Gly Leu Ser Asp Glu Pro Ile Ala Thr Thr Val Gln Asp Leu Asp Leu
       275                 280                 285

Arg Thr Val Gln Gly Ser Gln Asn Ala Ile Ser Val Ile Asp Ala Ala
       290                 295                 300

Leu Lys Tyr Val Asp Ser Gln Arg Ala Asp Leu Gly Ala Lys Gln Asn
305                 310                 315                 320

Arg Leu Ser His Ser Ile Asn Asn Leu Ala Asn Val Gln Glu Asn Val
               325                 330                 335

Asp Ala Ser Asn Ser Arg Ile Lys Asp Thr Asp Phe Ala Lys Glu Thr
           340                 345                 350

Thr Gln Met Thr Lys Ala Gln Ile Leu Gln Gln Ala Gly Thr Ser Ile
       355                 360                 365

Leu Ala Gln Ala Lys Gln Leu Pro Asn Ser Ala Met Ser Leu Leu
       370                 375                 380

<210> SEQ ID NO 9
<211> LENGTH: 1134
<212> TYPE: DNA
<213> ORGANISM: Vibrio vulnificus

<400> SEQUENCE: 9

```
atggcagtga atgtaaatac aaacgtagca gcaatgacag cacagcgtta cctgaataac    60
gcaaacagcg cacaacaaac ttcgatggag cgtctgtctt caggtttcaa aatcaacagt   120
gcaaaagatg acgcagccgg tctgcaaatc tctaaccgct gaacgtgca aagtcgcggt    180
ctagacgttg cggtacgtaa cgccaacgac ggtatctcaa tcgcacaaac cgcagaaggt   240
gcgatgaacg agaccaccaa catcctacaa cgtatgcgtg acctatctct gcaatcagcg   300
aacggctcaa actcaaaatc agagcgcgtg gcgattcaag aagagatcac cgcattgaac   360
gacgagctaa accgtatcgc agaaaccacg tcttttggtg gtaacaaact gctcaacggc   420
acttacggca cgaaagcaat gcaaattggt gcggataacg tgaagcggt catgctgtca    480
ctcaaagaca tgcgctctga caacgtgatg atgggcggcg tgagctacca agctgaagaa   540
ggcaaagaca agaactggaa tgtggccgca ggcgacaacg acttgacgat tgcactgaca   600
gacagctttg gtaacgagca agagatcgaa atcaacgcga agcgggcga tgacatcgaa    660
gagctagcga cgtacatcaa cggtcaaact gaccttgtaa agcgtcagt gggtgaaggc    720
ggcaagctac agatctttgc tggtaacaac aaagttcaag gtgaaattgc tttctcaggt   780
agcctagctg gtgaacttgg cctaggcgaa ggcaaaaacg tcacggtaga cacgattgac   840
gtgacaaccg tacaaggtgc gcaagagtcg gtagcgattg tggatgcggc actgaaatac   900
gtagacagcc accgtgcaga gctgggtgca ttccagaacc gtttcaacca tgcaatcagc   960
aacttggaca acatcaacga gaacgtgaac gcgtcgaaga gccgaatcaa agataccgac  1020
ttcgcgaaag aaacgactca gttgaccaag acacaaattc tatcgcaagc atcaagttcc  1080
attcttgcgc aagcgaaaca agcgccaaac tcagcgctaa gtctactagg ctaa        1134
```

<210> SEQ ID NO 10
<211> LENGTH: 377
<212> TYPE: PRT
<213> ORGANISM: Vibrio vulnificus

<400> SEQUENCE: 10

Met Ala Val Asn Val Asn Thr Asn Val Ala Ala Met Thr Ala Gln Arg
 1               5                  10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
            35                  40                  45

Gln Ile Ser Asn Arg Leu Asn Val Gln Ser Arg Gly Leu Asp Val Ala
 50                  55                  60

Val Arg Asn Ala Asn Asp Gly Ile Ser Ile Ala Gln Thr Ala Glu Gly
 65                  70                  75                  80

Ala Met Asn Glu Thr Thr Asn Ile Leu Gln Arg Met Arg Asp Leu Ser
                 85                  90                  95

Leu Gln Ser Ala Asn Gly Ser Asn Ser Lys Ser Glu Arg Val Ala Ile
                100                 105                 110

Gln Glu Glu Ile Thr Ala Leu Asn Asp Glu Leu Asn Arg Ile Ala Glu
            115                 120                 125

Thr Thr Ser Phe Gly Gly Asn Lys Leu Leu Asn Gly Thr Tyr Gly Thr
            130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Val Ser Tyr
                165                 170                 175

Gln Ala Glu Glu Gly Lys Asp Lys Asn Trp Asn Val Ala Ala Gly Asp
                180                 185                 190

Asn Asp Leu Thr Ile Ala Leu Thr Asp Ser Phe Gly Asn Glu Gln Glu
            195                 200                 205

Ile Glu Ile Asn Ala Lys Ala Gly Asp Asp Ile Glu Glu Leu Ala Thr
            210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
                260                 265                 270

Asn Val Thr Val Asp Thr Ile Asp Val Thr Thr Val Gln Gly Ala Gln
            275                 280                 285

Glu Ser Val Ala Ile Val Asp Ala Ala Leu Lys Tyr Val Asp Ser His
 290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
                340                 345                 350

Ile Leu Ser Gln Ala Ser Ser Ile Leu Ala Gln Ala Lys Gln Ala
            355                 360                 365

Pro Asn Ser Ala Leu Ser Leu Leu Gly
    370                 375

<210> SEQ ID NO 11
<211> LENGTH: 1127
<212> TYPE: DNA
<213> ORGANISM: Vibrio vulnificus

<400> SEQUENCE: 11
atggtttcac tcaataccaa cgtgtctgcg atggtcgctc agaggcatct gagcacagcg      60
gcaagtcagg tagctgaaac ccaaaaaaat ctaagttccg gattccgaat taatagtgcc     120
agcgatgatg ccgctggaat gcagatagcg aatacgcttc acgtccaaac ccgtggtttg     180

-continued

```
gatgtggcat taactaacgc tcatagtgct tatgctgttg cagaaacagc ggaaggggcg      240
ttggaagagg gcagtgaaat actgcagaga ttgcgatctc tttctcttca agccgcaaac      300
ggatcgaatt ctgatgagga tcggcaaagt ttgcagttgg aagtggtggt attgaaagat      360
gaagtggaaa gaatagccag gacaaccaca tttgcgggta aaaatctgtt tgatggaagt      420
tatggttcaa aaagttttca tcttggggca aattctaatt ccatttcttt gcaactcaaa      480
aacatgcgga ctcacgttcc tgagatgggc gggtatcatt accttgcctc ggagccagcg      540
gatgaggatt ggcaagttga caaggaatca aggcaactta gctttacttt tcgagatagc      600
gaaggggatg atcaatccat taagatctcg cttaagcctg agacagtct cgaagaagtc       660 gctacgtata tcaattcaca gcaaaatgtt gtggagtcct cggtgacgga tgatcggcga      720
ttgcagtttt atgtcgctaa tcgtcacgct cctgatggtt aaatatctc aggaagcttg       780 gagggagagc tagactttga accgcaagga caagtgacgc tcgatgaact cgatatcagt      840
agtgtgggtg gtgctcaatt ggcgattgct gttgttgata ctgcaattca atatctggat      900
tctcaccgaa gtgaaatcgg cagttttcaa atcgggtag aggggacgat ggacaatttg       960
caaagtatca atcgcaatgt cactgaatca aaagggcgaa tatgggatac cgattttgcg     1020
aaagcatcaa ccgctttagt gaagtctcag gtattgcaac aggctaccct tgccttgctg     1080
gctcaagcca agcaagcccc aggcagtgca attggattgc tatctta                   1127
```

<210> SEQ ID NO 12
<211> LENGTH: 375
<212> TYPE: PRT
<213> ORGANISM: Vibrio vulnificus

<400> SEQUENCE: 12

```
Met Val Ser Leu Asn Thr Asn Val Ser Ala Met Val Ala Gln Arg His
  1               5                  10                  15

Leu Ser Thr Ala Ala Ser Gln Val Ala Glu Thr Gln Lys Asn Leu Ser
             20                  25                  30

Ser Gly Phe Arg Ile Asn Ser Ala Ser Asp Asp Ala Ala Gly Met Gln
         35                  40                  45

Ile Ala Asn Thr Leu His Val Gln Thr Arg Gly Leu Asp Val Ala Leu
     50                  55                  60

Thr Asn Ala His Ser Ala Tyr Ala Val Ala Glu Thr Ala Glu Gly Ala
 65                  70                  75                  80

Leu Glu Glu Gly Ser Glu Ile Leu Gln Arg Leu Arg Ser Leu Ser Leu
                 85                  90                  95

Gln Ala Ala Asn Gly Ser Asn Ser Asp Glu Asp Arg Gln Ser Leu Gln
            100                 105                 110

Leu Glu Val Val Val Leu Lys Asp Glu Val Glu Arg Ile Ala Arg Thr
        115                 120                 125

Thr Thr Phe Ala Gly Lys Asn Leu Phe Asp Gly Ser Tyr Gly Ser Lys
    130                 135                 140

Ser Phe His Leu Gly Ala Asn Ser Asn Ser Ile Ser Leu Gln Leu Lys
145                 150                 155                 160

Asn Met Arg Thr His Val Pro Glu Met Gly Gly Tyr His Tyr Leu Ala
                165                 170                 175

Ser Glu Pro Ala Asp Glu Asp Trp Gln Val Asp Lys Glu Ser Arg Gln
            180                 185                 190

Leu Ser Phe Thr Phe Arg Asp Ser Glu Gly Asp Asp Gln Ser Ile Lys
        195                 200                 205
```

```
Ile Ser Leu Lys Pro Gly Asp Ser Leu Glu Glu Val Ala Thr Tyr Ile
    210                 215                 220

Asn Ser Gln Gln Asn Val Glu Ser Ser Val Thr Asp Arg Arg
225                 230                 235                 240

Leu Gln Phe Tyr Val Ala Asn Arg His Ala Pro Asp Gly Leu Asn Ile
                245                 250                 255

Ser Gly Ser Leu Glu Gly Glu Leu Asp Phe Glu Pro Gln Gly Gln Val
            260                 265                 270

Thr Leu Asp Glu Leu Asp Ile Ser Ser Val Gly Gly Ala Gln Leu Ala
        275                 280                 285

Ile Ala Val Val Asp Thr Ala Ile Gln Tyr Leu Asp Ser His Arg Ser
    290                 295                 300

Glu Ile Gly Ser Phe Gln Asn Arg Val Glu Gly Thr Met Asp Asn Leu
305                 310                 315                 320

Gln Ser Ile Asn Arg Asn Val Thr Glu Ser Lys Gly Arg Ile Trp Asp
                325                 330                 335

Thr Asp Phe Ala Lys Ala Ser Thr Ala Leu Val Lys Ser Gln Val Leu
            340                 345                 350

Gln Gln Ala Thr Ser Ala Leu Leu Ala Gln Ala Lys Gln Ala Pro Gly
        355                 360                 365

Ser Ala Ile Gly Leu Leu Ser
    370                 375

<210> SEQ ID NO 13
<211> LENGTH: 36
<212> TYPE: DNA
<213> ORGANISM: Artificial Sequence
<220> FEATURE:
<221> NAME/KEY: misc_feature
<222> LOCATION: 21..30
<223> OTHER INFORMATION: arbitrary primer 1; n may be a, t, g or c.

<400> SEQUENCE: 13
ggccacgcgt cgactagtca nnnnnnnnnn acgccc                             36

<210> SEQ ID NO 14
<211> LENGTH: 25
<212> TYPE: DNA
<213> ORGANISM: Artificial Sequence
<220> FEATURE:
<223> OTHER INFORMATION: specific primer 1

<400> SEQUENCE: 14
ttcttcacga ggcagacctc agcgc                                         25

<210> SEQ ID NO 15
<211> LENGTH: 20
<212> TYPE: DNA
<213> ORGANISM: Artificial Sequence
<220> FEATURE:
<223> OTHER INFORMATION: arbitrary primer 2

<400> SEQUENCE: 15
ggccaagagt cgactagtca                                               20

<210> SEQ ID NO 16
<211> LENGTH: 23
<212> TYPE: DNA
<213> ORGANISM: Artificial Sequence
<220> FEATURE:
<223> OTHER INFORMATION: specific primer 2

<400> SEQUENCE: 16
```

```
ccgcacttgt gtataagagt cag                                              23
```

<210> SEQ ID NO 17
<211> LENGTH: 864
<212> TYPE: DNA
<213> ORGANISM: Listeria monocytogenes flaA

<400> SEQUENCE: 17

```
atgaaagtaa atactaatat cattagcttg aaaacacaag aatatcttcg taaaaataac      60
gaaggcatga ctcaagcgca agaacgtttg catctggta  aacgtattaa cagttctctt     120
gatgacgctg ctggtcttgc agttgttact cgtatgaacg ttaaatctac aggcttagat     180
gcagcaagca aaaactcatc catgggtatt gacttgttac aaacagcgga ttcagctctt     240
agctccatga gttcaatctt gcaacgtatg cgtcaattag cagtacaatc ttctaacggt     300
tcattcagtg acgaagatcg taaacaatac actgctgaat cggtagctt  gatcaaagaa     360
cttgatcacg ttgctgacac tactaactac aacaacatca aattactaga tcaaactgct     420
acaggtgctg ctactcaagt aagcatccaa gcgtctgata agctaatga  cttaatcaat     480
atcgatcttt tcaatgcgaa aggtctttct gctggaacaa tcactttagg tagtggttct     540
acagttgctg gttatagtgc attatctgtt gctgatgctg attcttctca agaagcaacg     600
gaagctattg atgaattaat caataacatc tctaacggtc gtgcacttct aggtgctggt     660
atgagtcgcc ttagctacaa tgtatctaac gtgaacaacc aatccatcgc aactaaagca     720
tctgcttcct ctattgaaga tgcagatatg gctgctgaaa tgtccgaaat gactaaatac     780
aaaattctta cacaaacatc tatcagcatg ctttctcaag caaaccaaac accgcaaatg     840
ttaactcaat taattaacag ctaa                                             864
```

<210> SEQ ID NO 18
<211> LENGTH: 1488
<212> TYPE: DNA
<213> ORGANISM: Salmonella typhimurium fliC

<400> SEQUENCE: 18

```
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tatcgatctg     480
aagcagatca actctcagac cctgggtctg gatacgctga atgtgcaaca aaaatataag     540
gtcagcgata cggctgcaac tgttacagga tatgccgata ctacgattgc tttagacaat     600
agtacttta  aagcctcggc tactggtctt ggtggtactg accagaaaat tgatggcgat     660
ttaaaatttg atgatacgac tggaaaatat tacgccaaag ttaccgttac gggggga act     720
ggtaaagatg gctattatga gtttccgtt  gataagacga cggtgaggt  gactcttgct     780
ggcggtgcga cttccccgct tacaggtgga ctacctgcga cagcaactga ggatgtgaaa     840
aatgtacaag ttgcaaatgc tgatttgaca gaggctaaag ccgcattgac agcagcaggt     900
gttaccggca cagcatctgt tgttaagatg tcttatactg ataataacgg taaaactatt     960
```

-continued

```
gatggtggtt tagcagttaa ggtaggcgat gattactatt ctgcaactca aaataaagat   1020
ggttccataa gtattaatac tacgaaatac actgcagatg acggtacatc caaaactgca   1080
ctaaacaaac tgggtggcgc agacggcaaa accgaagttg tttctattgg tggtaaaact   1140
tacgctgcaa gtaaagccga aggtcacaac tttaaagcac agcctgatct ggcggaagcg   1200
gctgctacaa ccaccgaaaa cccgctgcag aaaattgatg ctgctttggc acaggttgac   1260
acgttacgtt ctgacctggg tgcggtacag aaccgtttca actccgctat taccaacctg   1320
ggcaacaccg taaacaacct gacttctgcc cgtagccgta tcgaagattc cgactacgcg   1380
accgaagttt ccaacatgtc tcgcgcgcag attctgcagc aggccggtac ctccgttctg   1440
gcgcaggcga accaggttcc gcaaaacgtc ctctctttac tgcgttaa               1488
```

MUCOSAL VACCINE ADJUVANTS CONTAINING BACTERIAL FLAGELLINS AS AN ACTIVE COMPONENT

TECHNICAL FIELD

The present invention relates to mucosal vaccine adjuvants containing flagellins, the structural component of bacterial flagella, originated from *Vibrio vulnificus, Salmonella typhimurium,* and Listeria *monocytogenes* as an active component.

BACKGROUND ART

The infectious disease from *Vibrio vulnificus* or its abbreviation "*V. vulnificus*" has a relatively short history, but clinical cases have been reported continuously worldwide and this disease is one of the newly obserbed diseases. Although the absolute number of clinical cases of this disease is less than that of cholera or salmonella food poisoning, it raises a significant social problem due to its high mortality rate and tragic clinical manifestations.

*V. vulnificus* was first reported in 1976 by Hollis et al. of CDC (Centers for Disease Control in USA) after they studied bacteriological properties of halophilic, pathogenic Vibrio that was isolated from human for 11 years, and named lactose-fermenting Vibrio or Lac(+) due to its feature of lactose fermenting. In 1979, Blake el al. of CDC classified 39 patients reported in CDC to primary septicemia and wound infection groups according to clinical manifestations analyzed by epidemiology (Blake, P. A., Merson M. H., Weaver, R. E., Hollis, D. G., Heublin, P. C., *N. EngL J. Med* 300:1-6, 1979). In the same year, Farmer named it *Vibrio vulnificus* (vulnus=wound, ficus=forming) as a new species. (Farmer, J. J. III, *Lancet* 2 :903, 1979).

Infections from pathogenic bacteria and viruses are progressed mostly through the mucosal route via aspiration, oral intake and sexual transmission etc. In adult, the surface area of respiratory, digestive, and genitourinary systems that covered by a mucosal surface is approximately 400 m$^2$. The primary defense system against normal flora and invasion of viruses and bacteria originated from the external environment relates mainly to the mucosal immune response. The mucosal immunity involved mainly in the mucosal surface has not yet been studied in depth in comparison to the systemic immunity, but there is no doubt about its importance. Recently, Professor Kiyono et al. from Tokyo University in Japan have studied it intensively. It is generally known that in case of vaccination via mucosal route, the mucosal immune response is more effectively induced than those via the intrademal or subcutaneous routes, and that the mucosal immune response is mediated mainly by immunoglobulin-A (Ig A).

Vaccination via the mucosal route has an advantage not only in enhancing a systemic immune response but also in enhancing a mucosal immune response simultaneously. For this reason, concerns are amplified on the studies for the development of preventive vaccines that induce effective immune responses in mucosal tissues. However the administration of protein antigens via the mucosal route has a disadvantage that immunogenicity is decreased compared to the administration via the systemic route. Therefore the most important factor in the development of mucosal vaccine is the development of an effective mucosal adjuvant that can be safely adminstered together with vaccine antigens.

One of the most important factors of a vaccine adjuvant is the possession of an immune control function, such as one that controls the expression of co-stimulating molecules of antigen presenting cells and the cytokine secretion induced by antigen specific T-cell induction. Nowadays substances that are in use or concerned as a vaccine adjuvant are mineral salts such as hydroxy aluminium gel, surfactants, substances originating bacteria, cytokine, hormone, polyanions, polyacryls, living vectors using carriers and viruses, and vehicles such as mineral oil or liposome. Among these, the most actively studied and noticed vaccine adjuvants are the protein originated mucosal vaccine adjuvants such as cholera toxin (CT) from *Vibrio cholerae* and the heat-labile toxin (LT) from *Escherichia coli.* It was reported that the administration of these vaccine adjuvants via the mucosal tissue route induces the production of antigen-specific antibodies in serum and mucosal tissue, and facilitates co-stimulatory signaling of T-cell induced by expression of B7-2 on the surface of antigen presenting cells. (Boyaka, P. N., Jackson, R. J., Kiyoni, H., Yuki, Y., McGhee, J. R. Immunol. 170:454-462, 2003; Kweon, M. N., Yamamoto, M., Watanabe, F., Tamura, S., Van Ginkel, F. W., Miyauchi, A., Takagi, H., Takeda, Y., Hamabata, T., Fujihashi, K., McGhee, J. R., Kiyono, H. J. Infect-.Dis. 186:1261-1269, 2002). However these adjuvants are exotoxins with high enterotoxicity, thus being inadequate to be used directly for human beings. Nowadays worldwide research is being performed with the purpose of making these less toxic but with higher adjuvancity.

DISCLOSURE OF INVENTION

Technical Problem

Under these circmustances, the present inventors discovered that the flagellin from *V. vulnificus,* which is an agonist of TLR-5, stimulates production of interleukin-8 (IL-8) from epithelial cells, matures human dendritic cells, and in case of mixing with tetanus toxoid and immunizing mice with it via the intranasal route 3 times, shows a more remarkable increasing mucosal IgA than in the case of administering tetanus toxoid only, and also found that this protects mice completely from lethal doses of tetanus toxoid. In addition, the present inventors found that the above effects are not limited to flagellins of *V. vulnificus,* but that the same protective immune effects are found in the flagellins of the *Salmonella typhimurium,* which is a Gram negative bacterium and has many flagella in a single bacterium, and in those of the *Listeria monocytogenes,* which is a Gram positive bacterium; and thereby completed the present invention.

Therefore, the object of the present invention is to provide mucosal vaccine adjuvants including flagellins, components of bacterial flagella, as an active component, which are necessary to develop various kinds of effective vaccines such as vaccines for infectious diseases, anticancer and contraception etc.

BRIEF DESCRIPTION OF THE DRAWINGS

FIG. 1 shows the locus 1 that is one of two operon structures of *V. vulnificus* flagellin gene.

FIG. 2 shows the locus 2 that is one of two operon structures of *V. vulnificus* flagellin gene.

FIG. 3 shows the result of completely protection of the host from lethal doses of tetanus toxin after immunization with 1 μg, 5 μg and 15 μg of FlaB mixed with the tetanus toxoid via mice transnasal route.

FIG. 4 shows the result of the antigen specific immune response measured by the ELISA method using sampled mice sera and various mucus samples after immunization with 1 μg, 5 μg and 15 μg of FlaB mixed with the tetanus toxoid via the mice transnasal route.

FIG. 5 shows the result of the antigen specific immune response measured by the ELISA method using mice sera after immunization with FlaA of Listeria, FlaB of *V. vulnificus*, and FliC of *Salmonella* mixed with the tetanus toxoid via the mice transnasal route.

FIG. 6 shows the secretion of interleukin-8 (IL-8) from epithelial cells in the dose dependent manners after administration with the recombinant FlaB to epithelial cells.

FIG. 7 shows the transcriptional activation of IL-8 and Nuclear factor kappa B when recombinant FlaB was administered to cells expressing the human TLR-5 and IL-8 transcriptional reporters, or to cells expressing the human TLR-5 and the nuclear factor kappa B.

FIG. 8 shows the transcriptional activation of IL-8 when fusion proteins of glutathion-S-transferase and 6 flagellins, the structural component of *V. vulnificus* flagella, were administered to the cells expressing the human TLR-5 and IL-8 transcriptional reporters.

FIG. 9 shows the induction of maturation of the dendritic cell when the recombinant *V. vulnificus* FlaB and the recombinant *Salmonellas* FliC were administered to the human dendritic cell.

BEST MODE FOR CARRYING OUT THE INVENTION

The present inventors isolated the flagellin flagellin proteins and subcutaneously injected mice with them (active immunization) to confirm the defensive immunities, and observed a formation of granulomatous lesions in mice skin tissues injected with flagellin proteins subcutaneously. With this result, we confirmed that the flagellin acts as a vaccine adjuvant.

The Flagella, an important factor for determining the mobility of bacteria, is composed of hooks, basal bodies and filaments in general. It is known that the flagella has various functions such as the swimming or swarming motility of bacteria, determining the taxis of bacteria, and forming the biofilm and determining the adhesiveness of bacteria (Mc-Carter, L. L., Microbiol Mol Biol Rev. 65:445-62, 2001; Kim, Y. K, McCarter, L. L., J Bacteriol. 182:3693-704, 2000; McCarter, L. L., J Bacteriol. 177:1595-609, 1995; Boles, B. R., McCarter, L. L. J Bacteriol. 182:1035-45, 2000; Prouty, M. G., Correa, N. E., Kiose, K. E. Mol Microbiol. 2001 March; 39(6):1595-609, 2001). *V. vulnificus* has a polar flagellum (McCarter, L. L., Microbiol Mol Biol Rev. 65:445-62, 2001). The structural component of flagella is named the flagellin, and this flagellin forms filaments assembled regularly. According to the result of recent study, it is known that mammalian TLR-5 (Toll-like receptor-5) recognizes flagellins of both Gram-negative and Gram-positive bacteria and subsequently activates the NF-κB pathway of host cells (Hayashi, F., Smith, K D., Ozinsky, A., Hwan, T. R., Yi, E. C., Goodlett, D. R., Eng, J. K., Akira, S., Underhill, D. M., Aderem, A., Nature 410:1099-1103, 2001). The TLR, a receptor recognizing molecular patterns associated with pathogens, acts as a major component of the first line innate immune system against various infectious pathogens, and is a celluar receptor associated with the stimulation of effective adaptive immune responses (Akira, S., Hemmi, H., Immunol. Lett. 85:85-95, 2003). Therefore, TLR agonists can be the target for developments of various vaccine adjuvants.

According to the research of our inventors, genes composing the flagellum of *V. vulnificus* are composed of the flaA expressed DNA sequence number 1 or amino acid sequence number 2, the flaB expressed DNA sequence number 3 or amino acid sequence number 4, the flaF expressed DNA sequence number 5 or amino acid sequence number 6, the flaC expressed DNA sequence number 7 or amino acid sequence number 8, the flaD expressed DNA sequence number 9 or amino acid sequence number 10, and the flaE expressed DNA sequence number 11 or amino acid sequence number 12; the constitution of each genes is similar to that of *Vibrio parahemotyticus*, and their homologies are also high.

Processes proving the effect of the vaccine adjuvant comprising the flagellin, the structural component of bacterial flagella, according to this invention are as follows:
1) Production and isolation of recombinant flagellins;
2) Measurement of the level of antigen specific immune responses after intranasal immunization with mixed recombinant flagellins and tetanus toxoids;
3) Measurement of the host defense ability against tetanus toxins after intranasal immunization with mixed recombinant flagellins and tetanus toxoids in mice;
4) Confirmation of enhanced production of IL-8 from epithelial cells with the recombinant flagellin;
5) Confirmation of induction of intracellular signal transduction after binding the recombinant flagellin and TLR-5;
6) Observation of the recombinant flagellin inducing the maturation of human DCs.

Therefore, the present invention relates to vaccine adjuvants containing flagellins, structural components of bacterial flagella, as an active component.

In addition, the present invention relates to a method of manufacturing recombinant mmunogens having the adjuvanticity induced by flagellin, which comprises substituting the genes encoding various immunogen epitopes for a part of the genes present between the N-terminal and the C-terminal of the structural genes of bacterial flagellins binding to TLR-5.

More specifically, the recombinant immunogens having the adjuvancity induced by the flagellin can be prepared by substituting the genes encoding protein antigen epitopes for the base sequences between the N-terminal regions of FlaA of amino acid sequence 1-191, FlaB of amino acid sequence 1-191, FlaF of amino acid sequence 1-191, FlaC of amino acid sequence 1-191, FlaD of amino acid sequence 1-191 and FlaE of amino acid sequence 1-189;

and the C-terminal regions of FlaA of amino acid sequence 277-376, FlaB of amino acid sequence 278-377, FlaF of amino acid sequence 278-377, FlaC of amino acid sequence 285-385, FlaD of amino acid sequence 278-377 and FlaE of amino acid sequence 276-375, among the structural components of *Vibrio vulnificus* set out in SEQ ID NO: 1 to SEQ ID NO: 12.

The protein antigen epitopes in the present invention are the tetanus toxoid, the immunogenic epitopes of influenza virus, the specific antigens to PspA (pneumococcal surface protein A) and sperm of Pneumococcus, and so on.

The vaccine adjuvant in the present invention can be formulated into an oral form such as solution, suspension or emulsion form in an aqeous or oil solvent, or dried powder type that is aseptic state before use, and dissolved in pyrogen free water at use, or can be formulated into a non-oral administration (for example, subcutaneous injection, intravenous injection or intramuscular injection).

In the oral formulation, it could be manufactured in various formulation by common methods using carrier or forming agent, for example, tablets, troches, aqueous or oily emulsions, powder or particles that can be sprayed, emulsions, soft or hard capsules, syrup or ellixir; which can be selected according to the unit dosage or form.

The non-oral formulation could be injected by forming of sterilized injectable solution or emulsions that suspended with non-toxic available diluents or solvents like 1, 2 butadiol. Examples of diluents or solvents that can be used are water, Ringer solution and isoosmotic physiologic salines, and common solvents like ethanol, polyethileneglycol and polyprophyleneglycol can also be used. Sterilized volatile oils can be used both as solvent or emulsion solvent. In a suppository form, the medications are administered by the intra-rectal route after formulation by mixing the medications with non-irritable excipients, for example cocoa butter or polyethyleneglycol, that are solid at normal temperature but liquid at rectal temperature.

The examples of the vaccine adjuvants in the present invention are adjuants for anti-toxin vaccines against tetanus etc.; live attenuated or killed vaccines against cholera, typhoid fever and so on; anti-viral vaccines against influenza, SARS, etc.; anti-cancer vaccines against uterine cervix cancer and so on; anti-sperm contraceptive vaccines; and adjuvants for recombinant vaccines, however it is not limited to these examples.

Further, the present invention is not limited to flagellin of *V. vulnificus*, it may be applied to other flagellated bacteria that have similar flagellin protein encoded flagellin genes to that of *V. vulnificus*.

MODE OF THE INVENTION

Well explain the present invention more in detail below, but it is not limited to examples.

Characteristics of strains and plasmids used in the present invention are described in Table 1. Each detailed characteristic and manufacturing method is described in corresponding examples and experimental examples.

TABLE 1

| Strains or Plasmids | Characteristics | Origin |
|---|---|---|
| *V. vulnificus* | | |
| CMCP6 | Clinical isolation, highly virulent | Inventors |
| MO6-24/O | Clinical isolation, highly virulent | Glenn Morris Jr. (Maryland University) |
| ATCC29307 | Type strain | Bought from ATCC |
| *Listeria monocytogens* | | |
| 10403S | Type strain | Lee, Hyun Chul (Chonnam Natl. University) |
| *Salmonella typhimurium* | | |
| 14028S | Type strain | Choy, Hyun E (Chonam Natl. University) |
| *Escherichia coli* | | |
| R2566 | F-λ-fhuA2[lon] ompT lacZ::T7 gene1 gal sulA11 (mcrC-mrr) I14::IS10R(mcr-73::miniTn 10-TetS)2R(zgb-210::Tn10) (TetS) endA1 [dcm] | New England Biolab |
| Plasmids | | |
| pTYB | IMPACT (Intein Mediated Purification with an Affinity Chitin-binding Tag) expression vetor, AmpR, 7,417 bp | New England Biolab |

<Culture and Storage of Each Strain>

The LB (Luria Bertani) media (Difco Co.) were used for strains of *E.coli, Salmonella* and *Listeria*, and the HI(heart infusion) media (Difco Co.) were used for culturing of *V. vuinificus* in the following examples and experiments. After cultivation of these strains, glycerol was added to become 50% solution and they were stored at −80° C. in a deep freezer.

EXAMPLE 1

Construction of Transposon Libraries

*V. vulnificus* MO6-24/O type strains (obtained from J. Glenn Morris, Division of Hospital Epidemiology, University of Maryland School of Medicine, USA) and mini-Tn5 lacZ1 containing *E. coli* SM10λpir strains (obtained from Kenneth N. Timmis, GBF National Research Center for Biotechnology, Braunschweig, Germany) were cultured overnight at 37° C., 210 rpm in a stirring incubator, each were inoculated with single colony at 10 ml of 2.5 HI(2.5% NaCl heart infusion) broth media and 20 ml of LB (containing 100 μg/ml of Ampicillin and 100 μg/ml of Kanamicin) broth media The following day these were centrifuged, and washed with antibiotic-free LB broth media and centrifuged two times, then suspended at 100 μl of new LB broth media. Each bacterial suspension of *E. coli* and *V. vulnificus* were mixed together and dropped on LB agar plate. After culturing it overnight at 37° C., 800 μl of new 2.5 HI broth media was added to the grown colonies on LB agar plate and the grown colonies was scraped carefully after using sterilized glass rods. This bacterial suspension was moved to a 1.5 ml plastic test tube and suspended until becoming homogenous state. The suspension was diluted to ¹/₁₀ and ¹/₁₀₀, then undiluted and the dilutes dropped on TCBS (thiosulfate citrate bile sucrose) agar plate containing 200 μg/ml of Kanamycin, spread until sufficiently penetrated, and cultured overnight at 37° C.

The following day only Vibrio colonies, grown on TCBS agar plate, were taken and inoculated on TCBS agar plate containing 300 μg/ml of Kanamycin using toothpicks, and overnight cultured at 37° C. The following day grown Vibrio colonies were inoculated on 96-wells culture plates, containing 100 μl of 2.5 HI with 200 μg/ml of Kanamycin, and cultured overnight at 37° C. without stirring. The following day 80 μl of 50% glycerol was added to each well, containing grown bacteria, and stored at −80° C. in a deep freezer. When used for the experiments, these were inoculated to 2.5 HI broth media and cultured as needed.

EXAMPLE 2

Screening of Transposon Mutant Clones that Lose otility.

Each clone, prepared in Example 1, of the *V. vulnificus* MO6-24/O transposon libraries was cultured overnight at 37° C., then inoculated to 0.3% agar containing semi-solid state HI (heart infusion) agar plates using sterilized toothpicks and cultured at 37° C. for 6 hours. Degrees of the motility of the bacteria were then determined by measuring the range of movement after growing the bacteria 3 transposon mutant clones that nearly completely lost motility were selected by screening procedures, and the experiment that would identify the mutant genes which insert transposons was progressed.

EXAMPLE 3

Identification of Flagellin Operon Genes

The cloning of genes nearby the transposon inserted region was carried out by screening the cosmid gene libraries, using DNA fragment as primer for amplification by arbitrary PCR methods. The amplification of DNA fragments nearby the transposon inserted site was used a two-step PCR amplification method. In the first PCR, the arbitrary primer 1 (5-GGC-CACGCGTCGACTAGTCANNNNNNNNNNACGCCC-3) of sequence number 13, and the mini-Tn5 lacZ1 specific primer 1 (5-TTCTTCACGAGGCAGACCTCAGCGC-3) of sequence number 14, were used. The first PCR was set as follows; denaturing them for 30 seconds (sec) at 94° C., annealing for 30 sec at 30° C., and elongating for 1 minute (min) 30 sec at 72° C., with 5 cycles; afterwords a further 30 cycle PCR reaction was performed by denaturing for 30 seconds (sec) at 94° C., and annealing for 30 sec at 45° C., and elongating for 2 min at 72° C., with 30 cycles. The second PCR reaction was peformed using the products of the first PCR as templates. In the second PCR, the arbitrary primer 2 (5-GGCCAAGAGTCGACTAGTCA-3) of sequence number 15, and the mini-Tn5 lacZ1 specific primer 2 (5-CCGCACT-TGTGTATAAGAGTCAG-3) of sequence number 16, were used. Reaction conditions were; denaturing for 30 sec at 94° C., annealing for 30 sec at 72° C., and elongating for 1 min 30 sec at 72° C., 30 cycles. These PCR products were electroporesed in agarose gel and the amplified DNA fragments was separated from the gel and their base sequences were determined. As a result of the described PCR reaction, 3 types of specific DNA fragments were anplified.

The result of determining the amplified DNA fragments and BLAST analyzing them with genes recorded at GeneBank databases of U.S. National Center for Biological Information showed identities with bcr, cheR and flgG genes of *Vibrio Parahemolyticus*. According to the result of the complete decoding of the genome sequence analysis of *V. vulnificus* by the inventors, the described genes were located at polar flagellar flagellin operon, as shown in FIGS. 1 and 2.

EXAMPLE 4

Manufacture and Purification of Recombinant Flagellin.

DNA fragments containing the ORF of flaB gene of *V. vulnificus*, fliC gene of *Salmonella* (sequence number 18) and flaA gene of Listeria (sequence number 17) were ligated into pTYB12 vector (New England Biolabs Inc.), intein fusion expression vector, to yield each plasmid pCMM250, pCMM251, pCMM252. Each plasmids was transformed into *E. coli* ER2566 by electroporation, and induced the expression by adding 0.5 mM 5-bormo-indol-3-chloroisopropyl-β-D-galactopyranoside(ITPG). According to the manufacturers' (New England Biolabs Inc.) instructions, Flab, FliC and FlaA proteins were purified from Intein fusion proteins by using Chitin bead columns and 1,4-dithiothreiol. The endotoxin contained in the separated FlaB, FliC and FlaA proteins was removed by using the AffinityPak™ Detoxigel™ Endotoxin Removing Gel (Pirece Inc. Rockgord, Ill.).

Using the above described method, ORFs of genes of flaA, flaB, flaF, flaC, flaD and flaE of *V. vulnificus* were ligated into pGEX4T-1 vector (pCMM244-flaB, pCMM245-flaA, pCMM247-flaD, pCMM248-flaE, pCMM249-flaF). According to the manufacturers' (Amersham Pharmacia) instruction, the glutathion-S-transferase fusion protein was purified.

EXPERIMENTAL EXAMPLE 1

Experiment of Mucosal Immune Adjuvanticity of the Re-combinant Flagellin

Seven-week-old female Balb/c mice were intranasally immunized three times with 20 µl of PBS (phosphate buffered saline), 3 µg of tetanus toxoid alone, or with combinations of 3 µ of tetanus toxoid and 1 µg, 5 µg and 15 µg of FlaB of *V. vulnificus,* at 7-day intervals. Seven days after the last immunization, saliva, vaginal wash and serum samples were collected from the immunized mice to assess TT-specific systemic immune responses and mucosal immune responses. These responses were measured by ELISA (Enzyme linked immuno sorbant assay) methods, and the mice that were vaccinated 3 times before were observed for 7 days after systemic administration of minimally 200 folds of lethal doses of tetanus toxoid. The results are shown in FIGS. 3 and 4.

As shown in FIG. 3, the mice of the control group immunized with PBS only—were all dead (100%) within 24 hours, and only the 17% of the group of mice intranasally immunized with tetanus toxoid (TT) only had survived. However 100% of group of mice immunized with a combination of tetanus toxoid and 1μ, 5μg or 15μg of FlaB of *V. vulnificus* (TT+Vv-FlaB) had survived. The survived mice of TT showed tonic paralyses, but the group of TT+Vv-FlaB showed the same features as normal mice.

As shown in FIG. 4, the degree of the antigen specific systemic immune response and mucosal immune response was higher in the group of TT+Vv-FlaB than that in the group of PBS only or TT.

To confirm which of these vaccine adjuvanticities were general for flagellins of other non-*V. vulnificus*-flagella, the same experiments were performed with purified FlaA recombinant protein, that is flagellin structural component of *Listeria monocytogenes,* the Gram(+) bacterium, and with FliC recombinant protein, that is flagellin structural component of *Salmonella typhimurium,* the Gram(−) bacterium. The results are shown in Table 2 and FIG. 5.

TABLE 2

| Groups | Protective immunity test (against tetanus toxoid) | Survival rate (7 days) |
|---|---|---|
| naive (n = 5) | + | 0% |
| TT (tetanus toxoid) only (n = 15) | + | 17% |
| TT + 7 μg Lm-FlaA (n = 5) | + | 100% |
| TT + 9 μg Vv-FlaB (n = 5) | + | 100% |
| TT + 12 μg St-FliC (n = 5) | + | 100% |

The data of Table 2 are results of administration of tetanus toxoid after intranasal immunization with the combination of FlaA of Listeria, FlaB of *V. vulnificus* and FliC of *Salmonella,* and tetanus toxoid. It is shown that these flagellin structural component proteins completely protect the host from lethal doses of tetanus toxoid.

In the results of Table 2 and FIG. 5, it was observed that flagellins from the above mentioned 3 types of strains had the same efficacy as a vaccine adjuvant.

From the results of FIG. 3, FIG. 4, FIG. 5 and Table 2, it was shown that the recombinant flagellin played a role as an effective vaccine adjuvant.

EXPERIMENTAL EXAMPLE 2

Responses of Flagellin to Epithelial Cells.

Caco-2 cells were seeded at $2.0 \times 10^5$/well in 24-well plates and maintained overnight in the DMEM supplemented with 10% fetal calf serum (FCS). The following day they were washed with fetal calf serum free DMEM twice and treated with different concentrations of recombinant Vv-FlaB for 3 hours without FCS supplementation, and the level of IL-8 released to supernatants was measured using ELISA kit (R&D systems Co.). IL-8 expression in the Caco-2 cells treated with Vv-FlaB was analyzed by the real-time RT-PCR analysis. Total RNA was isolated from the Vv-FlaB treated cells. The results are shown in FIG. 6. In FIG. 6, it is shown that the recombinant FlaB binds to the receptors at the surface of Caco-2 cells and transductes intraceullar signals and facilitates IL-8, which induces the neutrophils secreting important mediators for inflammation, in dose dependent manners.

EXPERIMENTAL EXAMPLE 3

Regulation of IL-8 Expression of Flagellin Mediated by TLR-5

Caco-2 cells seeded at $2.0 \times 10^5$/well in 24-well plates were transfected with a propriate amounts of expression plasmids, the reporter pIL-8-Luc or pNF-κB-Luc (obtained from professor Kim, Jeong Mok, Hanyang University Medical School) and p3Xflag-hTLR5 that encodes TLR-5 genes (obtained form Steven B. Mizel, Departments of Microbiology and Immunology, Wake Forest University School of Medicine, U.S.A). The levels of luciferase activity were normalized to the lacZsd expression using the control expression plasmid pCMV-β-ga (9BD Biosciences Clontech, Palo Alto, Calif.). Total amounts of expression vectors were kept constant by adding appropriate amounts of blank vector. 24 hours after transfection, the culture was replaced with fresh medium, containing each of recombinant FlaB of *V. vuinificus*, recombinant FliC of *Salmonella* and recombinant FlaA of Listeria, and FlaA, FlaB, FlaF, FlaC, FlaD and FlaE of *V. vulnificus* purified by IMPACT-CNTM system and co-adinistration of glutathion-S-transferase fusion protein. Some hours after being administered, the luciferase activity was assayed by a luminometer (MicroLumatPlus LB 96V, Berthold, Wilbad, Germany) to measure expression of IL-8, and the results are shown in FIG. 7 and FIG. 8.

The recombinant FlaB activated the expression of IL-8 and pNF-κB in dose dependent manners. It was also shown by other flagellar structural components of *V. vulnificus*, FlaA, FlaF, FlaC, FlaD and FlaE with somehow difference in degree.

EXPERIMENTAL EXAMPLE 4

Response of Recombinant FlaB to Dendritic Cells from Human Peripheral Blood.

The peripheral blood mononuclear cells (PBMC) were separated by centrifugation using Ficoll Paque PLUS (Amersham Inc.) from human peripheral blood. The magnetic beads identifying the CD14 that selectively expresses at myeloid cells in PBMC were reacted at 6-12° C. for 20 min. The CD14 positive cells were separated by the magnetic cell sorter. CD14 positive cells were added to RPMI media containing 10% of FCS and co administration of 50 ng/ml of GM-CSF and 50 ng/ml of IL-4, and cultured for 6 days to differentiate into immature dendritic cells. After differentiation, they were treated with recombinant FlaB prepared in Example 4, and flagellin FliC of *Salmonella*, in doses of 6 nM concentration and cultured for 24 hours. The influence of FlaB and FliC to differentiation of human dendritic cells was observed. The reason for administration of FliC is to determine whether the present invention can be wide in use.

Monoclonal antibody that recognizes CD80, CD83 and CD86, selectively expressed on the surface of dendritic cells, and which binds to FITC (fluorescein isothicyanate) or phycoerytbrin was treated. The expression level of the cell groups that show positive signals was measured using flow cytometry. FIG. 9 shows the sesult.

When human dendritic cells were treated with recombinant FlaB of *V. vulnificus*, the percent levels of CD80, CD83 and CD86 positivity, meaning the maturity of dendritic cells, were increased by 67.3%, 23.57% and 143.29%. These levels were more increased rates than those of the control group, which showed 15.29%, 0.82% and 1.5%. However CD14, selective expressed don myeloid cells, levels were more decreased in maturation. The flagellin FliC of *Salmonella* showed similar traces to FlaB.

INDUSTRIAL APPLICABILITY

As is shown in the above results, the FlaA, FlaB, FlaF, FlaC, FlaD and FlaE, which are the structural component of flagellin of *V. vulnificus*, and FliC, which is the structural component of flagellin of *Salmonella*, and FlaA, which is the structural component of flagellin of *Listeria*, stimulates release of IL-8 from epithelial cells and maturation of dendritic cells. They also increase an antigen specific immune response of the host to immunostimulants uses as a vaccine.

When mice were immunized by tetanus toxoid and the mentioned flagellins via the intranasal route, they showed a remarkable increase of IgA level against antigens compared to the control group that were not administered flagellin as an adjuvant. Further, the host was protected completely from tetanus toxoid. Especially in vaginal washing, the IgA levels increased tremendously increased, so it could be available for use as an adjuvant of contraceptal vaccine that selective to sperms.

The recombinant flagellin proteins of the present invention are also available as an effective adjuvant of vaccine against other infectious diseases and anticancer therapies.

The invention claimed is:

1. A mucosal vaccine adjuvant comprising isolated bacterial flagellins as an active component, wherein said flagellins are obtained from *Vibrio vulnificus*, wherein said *Vibrio vulnificus* flagellins are one or more selected from the group consisting of the peptides of SEQ ID NO: 2, SEQ ID NO: 4, SEQ ID NO: 6, SEQ ID NO: 8, SEQ ID NO: 10, and SEQ ID NO: 12.

2. The mucosal vaccine adjuvant according to claim 1, wherein said vaccine adjuvant is an adjuvant for vaccine selected from the group consisting of an anti-toxin vaccine; a live attenuated or killed vaccine, an anti-viral vaccine, an anti-cancer vaccine against uterine cervical cancer, an anti-sperm contraceptive vaccine, a recombinant protein, and peptide vaccine.

3. The mucosal vaccine adjuvant according to claim 2, wherein the anti-toxin vaccine is against tetanus toxoid; the live attenuated or killed vaccine is against cholera and/or typhoid fever, the anti-viral vaccine is against influenza and/or SARS.

* * * * *